(12) United States Patent
Luo et al.

(10) Patent No.: US 11,380,847 B2
(45) Date of Patent: Jul. 5, 2022

(54) THERMALLY ACTIVATED DELAYED FLUORESCENT MATERIAL, PREPARATION METHOD THEREOF, AND ELECTROLUMINESCENT DEVICE

(71) Applicant: Wuhan China Star Optoelectronics Semiconductor Display Technology Co., Ltd., Wuhan (CN)

(72) Inventors: Jiajia Luo, Wuhan (CN); Shuxing Yan, Wuhan (CN)

(73) Assignee: Wuhan China Star Optoelectronics Semiconductor Display Technology Co., Ltd., Wuhan (CN)

(*) Notice: Subject to any disclaimer, the term of this patent is extended or adjusted under 35 U.S.C. 154(b) by 331 days.

(21) Appl. No.: 16/641,291

(22) PCT Filed: Jan. 13, 2020

(86) PCT No.: PCT/CN2020/071737
§ 371 (c)(1),
(2) Date: Feb. 24, 2020

(87) PCT Pub. No.: WO2021/103298
PCT Pub. Date: Jun. 3, 2021

(65) Prior Publication Data
US 2021/0408392 A1  Dec. 30, 2021

(30) Foreign Application Priority Data
Nov. 27, 2019  (CN) .......................... 201911178329.6

(51) Int. Cl.
*H01L 29/08* (2006.01)
*H01L 51/00* (2006.01)
(Continued)

(52) U.S. Cl.
CPC ........ *H01L 51/0071* (2013.01); *C07D 265/38* (2013.01); *C09K 11/06* (2013.01);
(Continued)

(58) Field of Classification Search
CPC .... H01L 51/0071; C07D 265/38; C09K 11/06
See application file for complete search history.

(56) References Cited

U.S. PATENT DOCUMENTS

2013/0306945 A1* 11/2013 Seo ..................... H01L 51/5056
257/40
2014/0034930 A1*  2/2014 Seo ..................... H01L 51/0051
257/40

(Continued)

FOREIGN PATENT DOCUMENTS

CN    108503603 A    9/2018
CN    108695440 A   10/2018
(Continued)

OTHER PUBLICATIONS

Dias et al., "Photophysics of thermally activated delayed fluorescence molecules" (Year: 2017).*

Primary Examiner — Caleb E Henry
(74) Attorney, Agent, or Firm — Taft Stettinius & Hollister LLP

(57) ABSTRACT

The present invention provides at thermally activated delayed fluorescent material, including a compound composed of an acceptor A and a donor D, the compound having a following structural formula of Formula 1:

D-A                                    Formula 1, wherein the receptor A is selected from any one of following structural formulas:

(Continued)

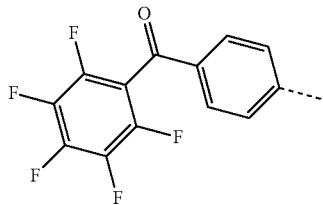

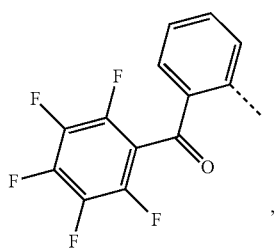

and the donor D has a following structural formula:

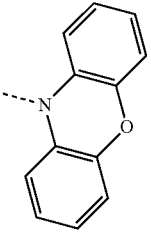

8 Claims, 2 Drawing Sheets (51) Int. Cl.
C07D 265/38 (2006.01)
C09K 11/06 (2006.01)
H01L 51/50 (2006.01)
(52) U.S. Cl.
CPC ............ C09K 2211/1007 (2013.01); C09K 2211/1018 (2013.01); H01L 51/5012 (2013.01); H01L 51/5016 (2013.01); H01L 51/5056 (2013.01); H01L 51/5072 (2013.01); H01L 51/5088 (2013.01); H01L 2251/552 (2013.01)

(56) References Cited

U.S. PATENT DOCUMENTS

| | | | |
|---|---|---|---|
| 2015/0340623 A1* | 11/2015 | Kawamura | C09K 11/06 257/40 |
| 2016/0028022 A1* | 1/2016 | Seo | C07D 403/14 257/40 |
| 2016/0093812 A1* | 3/2016 | Stoessel | H01L 51/0067 438/46 |
| 2018/0277765 A1* | 9/2018 | Yen | C07D 495/16 |
| 2019/0229270 A1* | 7/2019 | Yen | C07D 409/14 |
| 2021/0167304 A1* | 6/2021 | Scholz | C07F 7/0816 |

FOREIGN PATENT DOCUMENTS

CN 109817836 A 5/2019
WO 2014168101 A1 10/2014

* cited by examiner performing a reaction between a compound of A-X and a compound of D-H in a solution containing an alkali with catalyst at a first temperature for a first duration to obtain a reaction solution, wherein X is a halogen, A is selected from any one of the following structural formulas:

and D has a following structural formula:

S1 cooling the reaction solution to a second temperature to obtain a mixture; and

S2 separating the thermally activated delayed fluorescent material from the mixture, wherein the compound is composed of an acceptor A and a donor D, and the compound has a following structural formula of Formula 1:

D-A    Formula 1.

THERMALLY ACTIVATED DELAYED FLUORESCENT MATERIAL, PREPARATION METHOD THEREOF, AND ELECTROLUMINESCENT DEVICE

CROSS-REFERENCE TO RELATED APPLICATIONS

This application is a U.S. National Phase of International PCT Application No. PCT/CN2020/071737 filed Jan. 13, 2020, which claims the benefit of Chinese Patent Application Serial No. 201911178329.6 filed Nov. 27, 2019, the contents of each application are incorporated herein by reference in their entirety.

BACKGROUND OF INVENTION

Field of Invention

The present invention relates to a field of display technology, and particularly to a thermally activated delayed fluorescence (TADF) material, a preparation method thereof, and an electroluminescent device.

Description of Prior Art

It is known that organic light-emitting diodes (OLEDs) have attracted attention from many researchers, due to their huge application prospects and advantages, such as self-illumination without the need for a backlight, high luminous efficiency, wide viewing angles, fast response speed, a large temperature adaptation range, relatively simple production and processing techniques, low driving voltage, low energy consumption, lightness, thinness, flexibility, and so on.

A conventional OLED display device generally includes a substrate, an anode disposed on the substrate, an organic light-emitting layer disposed on the anode, an electron transport layer disposed on the organic light-emitting layer, and a cathode disposed on the electron transport layer. During operation, holes from the anode and electrons from the cathode are emitted to the organic light-emitting layer, and these electrons and holes are combined to generate an excited electron-hole pairs, and the excited electron-hole pairs are converted from an excited state to a ground state to achieve light-emitting.

In OLEDs, a dominant luminescent guest material is critical. Guest luminescent materials for early OLEDs are fluorescent materials. Because the ratio of excitons in a singlet energy state and excitons in a triplet energy state in the OLED is 1:3, the theoretical internal quantum efficiency (IQE) of fluorescent-based OLEDs can merely reach 25%, thus considerably limiting the application of fluorescent electroluminescent devices. Heavy metal complex phosphorescent materials can achieve 100% IQE by using the excitons in the singlet energy state and the excitons in the triplet energy state due to a spin-orbit coupling of heavy atoms. However, heavy metals commonly employed are precious metals, such as Ir, Pt, and the like, and the heavy metal complex phosphorescent materials have yet to be developed in fields of blue light materials.

Through a molecular design, pure organic thermally activated delayed fluorescence (TADF) materials can have a small minimum energy state difference ($\Delta E_{ST}$) between the singlet energy state and the triplet energy state, so that the excitons in the triplet energy state can be returned by reverse intersystem crossing (RISC) back to the singlet energy state, then to a ground state by a radiation transition to emit light, and thereby simultaneously use the excitons in the singlet energy state and in the triplet energy state, and 100% IQE may also be achieved.

For TADF materials, fast reverse intersystem-crossing (kRISC) and high photoluminescence quantum yield (PLQY) are necessary conditions for preparing high-efficiency OLEDs. At present, TADF materials with the above conditions are still relatively scarce compared to heavy metal Ir complexes. Because TADF materials have very wide spectrums and exciton lifetimes of microseconds, their applications in mass-produced device structures are greatly limited.

In view of above, there is an urgent need to develop a thermally activated delayed fluorescence (TADF) material as a host of a green light-emitting guest. Using 100% of the internal quantum efficiency of the TADF material, a fluorescent device can achieve efficiency of a phosphorescent device, while solving the problems of excessively broad spectrum and long exciton life, such that an effective path to break blockade of UDC patents in phosphorescent heavy metal complex can be achieved.

SUMMARY OF INVENTION

An object of the present invention is to provide a thermally activated delayed fluorescence (TADF) material as a host of a green light-emitting guest, and using 100% of the internal quantum efficiency of the TADF material, a fluorescent device can achieve efficiency of a phosphorescent device, while solving the problems of excessively broad spectrum and long exciton life, thereby overcoming the problem of color gamut difference when directly using the TADF light-emitting material, such that blockade of UDC patents in phosphorescent heavy metal complex can be broken, and cost is significantly reduced. Therefore, a series of high-performance TADF organic light-emitting diodes (OLEDs) can be prepared by using the light-emitting materials provided by the present invention.

In order to achieve the above object, the present invention provides a thermally activated delayed fluorescence (TADF) material, which includes a compound composed of an acceptor A and a donor D, the compound having a following structural formula of Formula 1:

$$D\text{-}A \qquad \text{Formula 1,}$$

wherein the receptor A is selected from any one of following structural formulas:

and the donor D has a following structural formula:

The present invention also provides a method of preparing a thermally activated delayed fluorescent material, including the following steps:

Step S1: performing a reaction between a compound of A-X and a compound of D-H in a solution containing an alkali with catalyst at a first temperature for a first duration to obtain a reaction solution, wherein X is a halogen, A is selected from any one of the following structural formulas:

and D has a following structural formula:

Step S2: cooling the reaction solution to a second temperature to obtain a mixture; and Step S3: separating the thermally activated delayed fluorescent material from the mixture, wherein the compound is composed of an acceptor A and a donor D, and the compound has a following structural formula of Formula 1:

D-A    Formula 1.

According to an embodiment of the present invention, the first temperature is 120° C., and the first duration is 48 hours.

According to an embodiment of the present invention, the second temperature is room temperature.

According to an embodiment of the present invention, in the step S1, the solution containing the alkali is toluene, the alkali is sodium tert-butoxide, and the catalyst includes acetic acid palladium and tri-tert-butylphosphine tetrafluoroborate.

According to an embodiment of the present invention, the step S2 further includes extracting the reaction solution several times with dichloromethane and combining organic extracts to obtain the mixture.

According to an embodiment of the present invention, in the step S3, the separating is performed by column chromatography with an eluent of methylene chloride and n-hexane in a volume ratio of 1:1.

According to an embodiment of the present invention, the step S1 is performed under an inert environment.

The present invention further provides an electroluminescent device, including: a base layer; a hole injection layer disposed on the base layer; a hole transport layer disposed on the hole injection layer; a light-emitting layer disposed on the hole transport layer; an electron transport layer disposed on the light-emitting layer; and a cathode layer disposed on the electron transport layer, wherein the light-emitting layer includes the thermally activated delayed fluorescent material according to the present invention.

According to an embodiment of the present invention, the base layer is made of a material including ITO; the injection layer is made of a material including 2,3,6,7,10,11-hexacyano-1,4,5,8,9,12-hexaazabenzophenanthrene; the hole transport layer is made of a material including 4,4',4''-tris(carbazole-9-yl)triphenylamine; the electron transport layer is made of a material including 1,3,5-tris(3-(3-pyridyl)phenyl)benzene(Tm3PyPB); and the cathode layer is made of a material including lithium fluoride and aluminum.

An object of the present invention is to provide a thermally activated delayed fluorescence (TADF) material as a host of a green light-emitting guest, and using 100% of the internal quantum efficiency of the TADF material, a fluorescent device can achieve efficiency of a phosphorescent device, while solving the problems of excessively broad spectrum and long exciton life, thereby overcoming the problem of color gamut difference when directly using the TADF light-emitting material, such that blockade of UDC patents in phosphorescent heavy metal complex can be broken, and cost is significantly reduced. Therefore, a series of high-performance TADF organic light-emitting diodes (OLEDs) can be prepared by using the light-emitting materials provided by the present invention.

BRIEF DESCRIPTION OF DRAWINGS

In order to more clearly illustrate the embodiments or the technical solutions of the existing art, the drawings illustrating the embodiments or the existing art will be briefly described below. Obviously, the drawings in the following description merely illustrate some embodiments of the present invention. Other drawings may also be obtained by those skilled in the art according to these figures without paying creative work.

DETAILED DESCRIPTION OF PREFERRED EMBODIMENTS

In order to make the above content of the present invention more comprehensible, preferred embodiments are described in detail below with detailed description in conjunction with the accompanying drawings.

An embodiment of the present invention provides a thermally activated delayed fluorescence (TADF) material as a host of a green light-emitting guest, and using 100% of the internal quantum efficiency of the TADF material, a fluorescent device can achieve efficiency of a phosphorescent device, while solving the problems of excessively broad spectrum and long exciton life, thereby overcoming the problem of color gamut difference when directly using the TADF light-emitting material, such that blockade of UDC patents in phosphorescent heavy metal complex can be broken, and cost is significantly reduced. Therefore, a series of high-performance TADF organic light-emitting diodes (OLEDs) can be prepared by using the light-emitting materials provided by the present invention.

Figure 1:
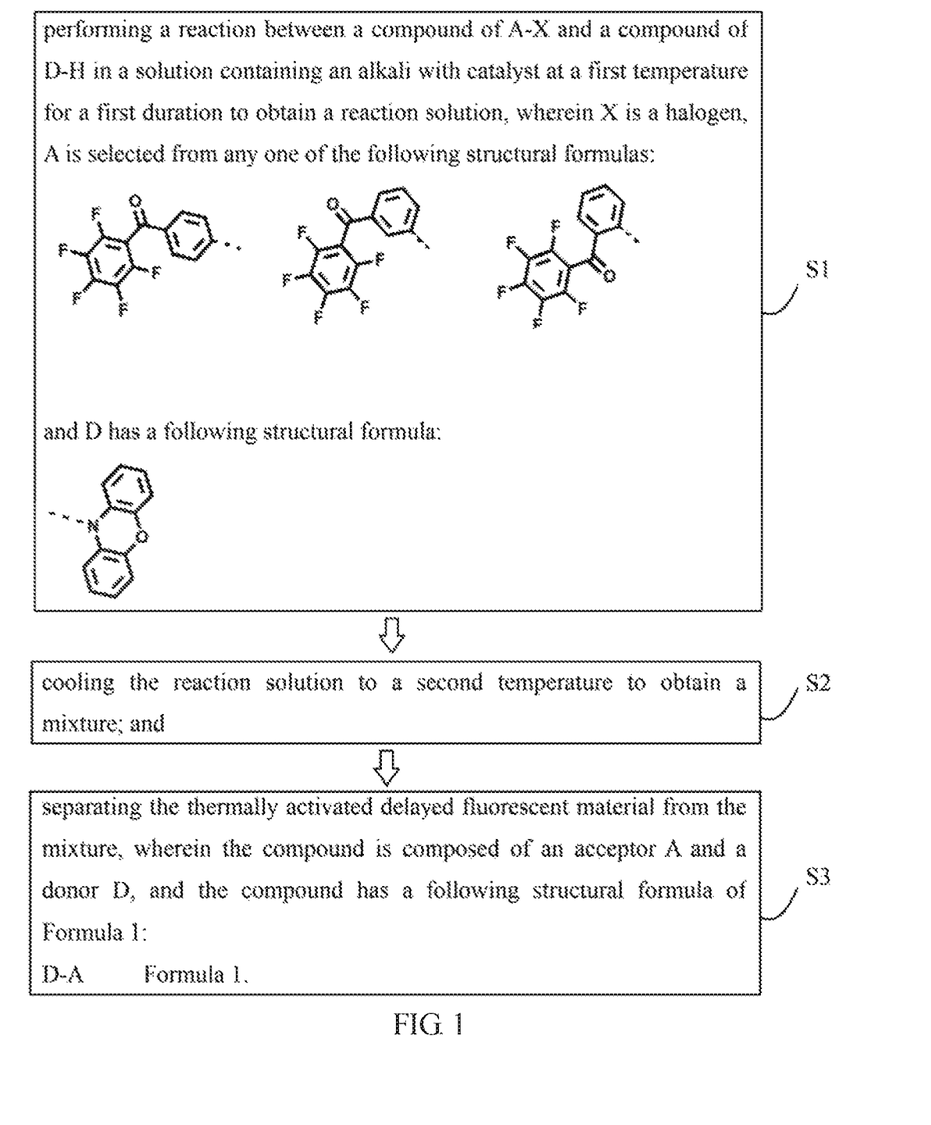
FIG. 1 is a flowchart of a method of preparing a thermally activated delayed fluorescence (TADF) material according to an embodiment of the present invention.

In order to achieve the above object, the present invention provides a thermally activated delayed fluorescence (TADF) material, which includes a compound composed of an acceptor A and a donor D, the compound having a following structural formula of Formula 1:

D-A        Formula 1, wherein the receptor A is selected from any one of following structural formulas:

and the donor D has a following structural formula:

Referring to FIG. 1, FIG. 1 is a flowchart of a method of preparing a thermally activated delayed fluorescence (TADF) material according to an embodiment of the present invention. As shown in FIG. 1, the present invention also provides a method of preparing a thermally activated delayed fluorescence (TADF) material, including the following steps:

Step S1: performing a reaction between a compound of A-X and a compound of D-H in a solution containing an alkali with catalyst at a first temperature for a first duration to obtain a reaction solution, wherein X is a halogen, A is selected from any one of the following structural formulas:

-continued and D has a following structural formula:

Step S2: cooling the reaction solution to a second temperature to obtain a mixture; and Step S3: separating the thermally activated delayed fluorescent material from the mixture, wherein the compound is composed of an acceptor A and a donor D, and the compound has a following structural formula of Formula 1:

D-A  Formula 1.

According to an embodiment of the present invention, the first temperature is 120° C., and the first duration is 48 hours.

According to an embodiment of the present invention, the second temperature is room temperature.

According to an embodiment of the present invention, in the step S1, the solution containing the alkali is toluene, the alkali is sodium tert-butoxide, and the catalyst includes acetic acid palladium and tri-tert-butylphosphine tetrafluoroborate.

According to an embodiment of the present invention, the step S2 further includes extracting the reaction solution several times with dichloromethane and combining organic extracts to obtain the mixture.

According to an embodiment of the present invention, in the step S3, the separating is performed by column chromatography with an eluent of methylene chloride and n-hexane in a volume ratio of 1:1.

According to an embodiment of the present invention, the step S1 is performed under an inert environment.

The present invention further provides an electroluminescent device, including: a base layer; a hole injection layer disposed on the base layer; a hole transport layer disposed on the hole injection layer; a light-emitting layer disposed on the hole transport layer; an electron transport layer disposed on the light-emitting layer; and a cathode layer disposed on the electron transport layer, wherein the light-emitting layer includes the thermally activated delayed fluorescent material according to the present invention.

According to an embodiment of the present invention, the base layer is made of a material including ITO; the injection layer is made of a material including 2,3,6,7,10,11-hexacyano-1,4,5,8,9,12-hexaazabenzophenanthrene; the hole transport layer is made of a material including 4,4',4"-tris(carbazole-9-yl)triphenylamine; the electron transport layer is made of a material including 1,3,5-tris(3-(3-pyridyl)phenyl)benzene(Tm3PyPB); and the cathode layer is made of a material including lithium fluoride and aluminum.

Example 1

In a specific Example 1 of the present invention, the target thermally activated delayed fluorescence (TADF) material to be synthesized includes Compound 1 having the following structural formula:

Compound 1

The compound 1 is synthesized by the following Reaction Scheme 1:

Reaction Scheme 1

Detailed synthetic steps of Compound 1 are as follows:

Raw Material 1 (1.75 g, 5 mmol), phenoxazine (1.10 g, 6 mmol), palladium acetate (45 mg, 0.2 mmol), and tri-tert-butylphosphine tetrafluoroborate (0.17 g, 0.6 mmol) were added to a 100 mL two-necked flask, then sodium tert-butylate (NaOtBu) (0.58 g, 6 mmol) was added thereto in a glove box, and then 40 mL of dehydrated and deoxygenated toluene was injected therein under an argon atmosphere to perform a reaction at 120° C. for 48 hours, followed by cooling the reaction solution to room temperature. After that, the reaction solution was poured into 200 mL of ice-water, followed by extraction three times with dichloromethane, and the organic extracts were combined, and separated and purified using silica gel column chromatography (dichloromethane:n-hexane, v:v, 1:1), such that 1.8 g of a blue-white powder was obtained with a yield of 79%. 1H NMR (300 MHz, CD2Cl2, δ): 7.71 (d, J=7.2 Hz, 2H), 7.14 (d, J=6.9 Hz, 2H), 7.08 (d, J=6.6 Hz, 2H), 7.06-6.93 (m, 6H). MS (EI) m/z: [M]+ calcd for C25H12F5NO2, 453.08; found, 453.00.

Example 2

In a specific Example 2 of the present invention, the target thermally activated delayed fluorescence (TADF) material to be synthesized includes Compound 2 having the following structural formula:

Compound 2

The compound 1 is synthesized by the following Reaction Scheme 2:

Reaction Scheme 2

Detailed synthetic steps of Compound 2 are as follows:
Raw Material 2 (1.75 g, 5 mmol), phenoxazine (1.10 g, 6 mmol), palladium acetate (45 mg, 0.2 mmol), and tri-tert-butylphosphine tetrafluoroborate (0.17 g, 0.6 mmol) were added to a 100 mL two-necked flask, then sodium tert-butylate (NaOtBu) (0.58 g, 6 mmol) was added thereto in a glove box, and then 40 mL of dehydrated and deoxygenated toluene was injected therein under an argon atmosphere to perform a reaction at 120° C. for 48 hours, followed by cooling the reaction solution to room temperature. After that the reaction solution was poured into 200 mL of ice-water, followed by extraction three times with dichloromethane, and the organic extracts were combined, and separated and purified using silica gel column chromatography (dichloromethane:n-hexane, v:v, 1:1), such that 1.6 g of a blue-white powder was obtained with a yield of 70%. 1H NMR (300 MHz, CD2Cl2, δ): 7.45 (s, 1H), 7.40-7.27 (m, 3H), 7.14 (d, J=6.6 Hz, 2H), 7.06-6.93 (m, 6H). MS (EI) m/z: [M]+ calcd for C25H12F5NO2, 453.08; found, 453.03.

Example 3

In a specific Example 3 of the present invention, the target thermally activated delayed fluorescence (TADF) material to be synthesized includes Compound 3 having the following structural formula:

Compound 3

The compound 1 is synthesized by the following Reaction Scheme 3:

Reaction Scheme 3

Detailed synthetic steps of Compound 3 are as follows:
Raw Material 3 (1.75 g, 5 mmol), phenoxazine (1.10 g, 6 mmol), palladium acetate (45 mg, 0.2 mmol), and tri-tert-butylphosphine tetrafluoroborate (0.17 g, 0.6 mmol) were added to a 100 mL two-necked flask, then sodium tert-butylate (NaOtBu) (0.58 g, 6 mmol) was added thereto in a glove box, and then 40 mL of dehydrated and deoxygenated toluene was injected therein under an argon atmosphere to perform a reaction at 120° C. for 48 hours, followed by cooling the reaction solution to room temperature. After that the reaction solution was poured into 200 mL of ice-water, followed by extraction three times with dichloromethane, and the organic extracts were combined, and separated and purified using silica gel column chromatography (dichloromethane:n-hexane, v:v, 1:1), such that 1.0 g of a blue-white powder was obtained with a yield of 44%. 1H NMR (300 MHz, CD2Cl2, δ): 7.70 (d, J=6.3 Hz, 1H), 7.48 (t, J=6.9 Hz, 1H), 7.28 (t, J=6.9 Hz, 1H), 7.18 (t, J=7.2 Hz, 1H), 7.14 (d, J=6.6 Hz, 2H), 7.06-6.93 (m, 6H). MS (EI) m/z: [M]+ calcd for C25H12F5NO2, 453.08; found, 453.01.

Figure 2:
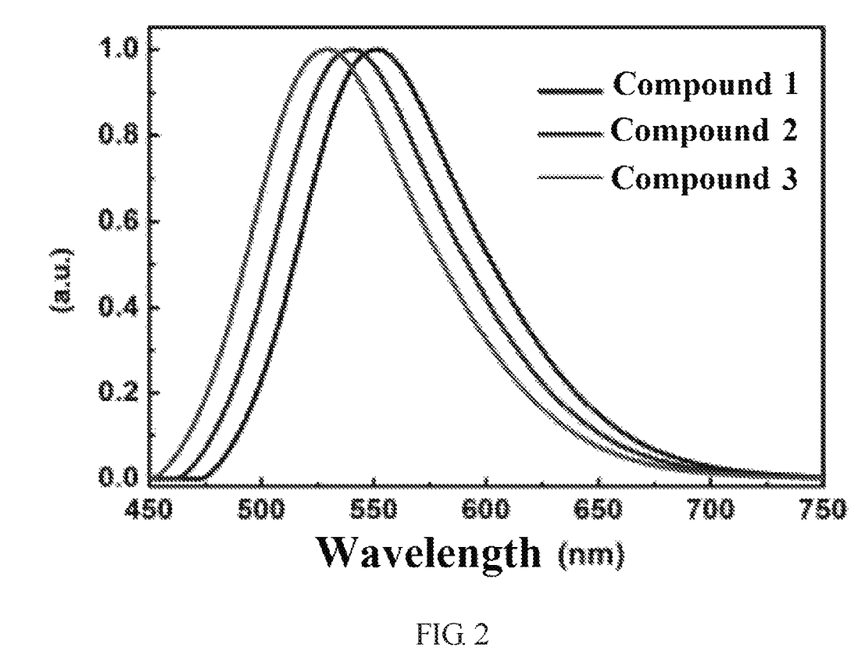
FIG. 2 is a fluorescence emission spectrum diagram of Compound 1, Compound 2, and Compound 3 in Examples 1, 2, and 3 of the present invention.

Specifically, Compound 1, Compound 2, and Compound 3 are analyzed, and the fluorescence emission spectrum of Compound 1, Compound 2, and Compound 3 as a pure film is shown in FIG. 2. The lowest singlet state (S1) and lowest triplet energy level (T1) of Compound 1, Compound 2, and Compound 3 were calculated based on B3LYP theory, and the highest occupied molecular orbital (HOMO) and the lowest unoccupied molecular orbital (LUMO) were detected. The obtained electrochemical energy is shown in Table 1 below:

TABLE 1

| | PL Peak (nm) | $S_1$ (eV) | $T_1$ (eV) | $E_{ST}$ (eV) | HOMO (eV) | LUMO (eV) |
|---|---|---|---|---|---|---|
| Compound 1 | 531 | 2.34 | 2.30 | 0.04 | −5.42 | −2.28 |
| Compound 2 | 542 | 2.29 | 2.28 | 0.01 | −5.41 | −2.28 |
| Compound 3 | 549 | 2.26 | 2.24 | 0.02 | −5.44 | −2.28 |

PL peak is the photoluminescence peak, S1 is the lowest singlet energy level, T1 is the lowest triplet energy level, ΔEST is the energy level difference between the lowest singlet energy level and the lowest triplet energy level, HOMO is the highest occupied molecular orbital, and LUMO is the lowest unoccupied molecular orbital.

As can be known from FIG. 2 and Table 1, Compound 1, Compound 2, and Compound 3 of Example 1, Example 2, and Example 3 of the present invention satisfy the performance requirements.

Furthermore, an embodiment of the present invention also provides an electroluminescent device including the above-described thermally activated delayed fluorescent (TADF) material.

Figure 3:
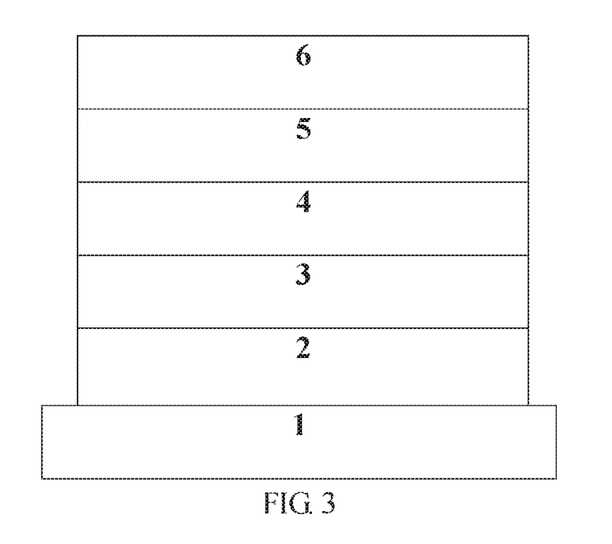
FIG. 3 is a schematic structural diagram of an electroluminescent device according to an embodiment of the present invention.

Referring to FIG. 3, in particular, the electroluminescent device 100 includes: a substrate layer 1; a hole injection layer 2 disposed on the substrate layer 1; a hole transport layer 3 disposed on the hole injection layer 2; a light-emitting layer 4 disposed on the hole transport layer 3; an electron transport layer 5 disposed on the light-emitting layer 4; and a cathode layer 6 disposed on the electron transport layer 5, wherein the light-emitting layer 4 includes the thermally activated delayed fluorescent (TADF) material.

According to an embodiment of the invention, in the electroluminescent device, the base layer is made of material including ITO; the hole injection layer is made of material including 2,3,6,7,10,11-hexacyano-1,4,5,8,9,12-hexaazatriphenylene; the hole transport layer 3 is made of material including 44,4',4''-Tris(carbazol-9-yl)-triphenylamine (TCTA); the electron transport layer 5 is made of material including 1,3,5-tris(3-(3-pyridyl)phenyl)benzene (Tm3PyPB); and the cathode layer is made of material including lithium fluoride and aluminum.

Specifically, Compound 1, Compound 2, and Compound 3 are used as the light-emitting layers 4 to manufacture Device 100, Device 200, and Device 300, respectively, and performance of Device 100, Device 200, and Device 300 was measured. In each of Device 100, Device 200, and Device 300 is 2 nm, a thickness of each of the base layer 1 and the hole injection layer 2 is 2 nm, and a thickness of the hole transport layer 3 is 35 nm. The light-emitting layer 4 of Device 100, Device 200, and Device 300 includes 7% of Compound 1, Compound 2, and Compound 3, respectively, and has a thickness of 40 nm. A thickness of the electron transport layer 5 is 40 nm, and in the cathode 6, a thickness of lithium fluoride is 1 nm, and a thickness of aluminum is 100 nm.

The current-brightness-voltage characteristics of Device 100, Device 200, and Device 300 were further measured by a Keithley source measurement system (Keithley 2400 Sourcemeter, Keithley 2000 Currentmeter) with a calibrated silicon photodiode. The electroluminescence spectrum was measured by a French JY SPEX CCD3000 spectrometer. All measurements were conducted at room temperature under ambient atmosphere. The performance data of Device 100, Device 200, and Device 300 is shown in Table 2 below, and Device 100, Device 200, and Device 300 meet the performance requirements.

TABLE 1

| Device | Maximum current efficiency (cd/A) | CIEy | maximum external quantum efficiency (%) |
|---|---|---|---|
| Device 100 | 86.7 | 0.25 | 34.1% |
| Device 200 | 77.5 | 0.25 | 30.8% |
| Device 300 | 64.3 | 0.25 | 28.9% |

Accordingly, an embodiment of the present invention provides a thermally activated delayed fluorescence (TADF) material as a host of a green light-emitting guest, and using 100% of the internal quantum efficiency of the TADF material, a fluorescent device can achieve efficiency of a phosphorescent device, while solving the problems of excessively broad spectrum and long exciton life, thereby overcoming the problem of color gamut difference when directly using the TADF light-emitting material, such that blockade of UDC patents in phosphorescent heavy metal complex can be broken, and cost is significantly reduced. Therefore, a series of high-performance TADF organic light-emitting diodes (OLEDs) can be prepared by using the light-emitting materials provided by the present invention.

While the invention has been described by way of example and in terms of the preferred embodiments, it is to be understood that the invention is not limited to the disclosed embodiments. To the contrary, it is intended to cover various modifications and similar arrangements. Therefore, the scope of the appended claims should be accorded the broadest interpretation so as to encompass all such modifications and similar arrangements.

What is claimed is:
1. An electroluminescent device, comprising:
a base layer;
a hole injection layer disposed on the base layer;
a hole transport layer disposed on the hole injection layer;
a light-emitting layer disposed on the hole transport layer;
an electron transport layer disposed on the light-emitting layer; and
a cathode layer disposed on the electron transport layer,
wherein the light-emitting layer comprises a thermally activated delayed fluorescent material, the thermally activated delayed fluorescent material comprises a compound composed of an acceptor A and a donor D, the compound having a following structural formula of Formula 1:

D-A Formula 1, wherein the acceptor A is selected from any one of following structural formulas:

and the donor D has a following structural formula:

wherein the base layer is made of a material comprising ITO, the injection layer is made of a material comprising 2,3,6,7,10,11-hexacyano-1,4,5,8,9,12-hexaazabenzophenanthrene; the hole transport layer is made of a material comprising 4,4',4"-tris(carbazole-9-yl)triphenylamine; the electron transport layer is made of a material comprising 1,3,5-tris(3-(3-pyridyl)phenyl)benzene(Tm3PyPB); and the cathode layer is made of a material comprising lithium fluoride and aluminum.

2. A method of preparing a thermally activated delayed fluorescent material, comprising the following steps:
Step S1: performing a reaction between a compound of A-X and a compound of D-H in a solution containing an alkali with catalyst at a first temperature for a first duration to obtain a reaction solution, wherein X is a halogen, A is selected from any one of the following structural formulas:

and D has a following structural formula:

Step S2: cooling the reaction solution to a second temperature to obtain a mixture; and
Step S3: separating the thermally activated delayed fluorescent material from the mixture, wherein the compound is composed of an acceptor A and a donor D, and the compound has a following structural formula of Formula 1:

D-A Formula 1.

3. The method of preparing the thermally activated delayed fluorescent material according to claim 2, wherein the first temperature is 120° C., and the first duration is 48 hours.

4. The method of preparing the thermally activated delayed fluorescent material according to claim 2, wherein the second temperature is room temperature.

5. The method of preparing a thermally activated delayed fluorescent material according to claim 2, wherein in the step S1, the solution containing the alkali is toluene, the alkali is sodium tert-butoxide, and the catalyst comprises acetic acid palladium and tri-tert-butylphosphine tetrafluoroborate.

6. The method of preparing the thermally activated delayed fluorescent material according to claim 2, wherein the step S2 further comprises extracting the reaction solution several times with dichloromethane and combining organic extracts to obtain the mixture.

7. The method of preparing the thermally activated delayed fluorescent material according to claim 2, wherein in the step S3, the separating is performed by column chromatography with an eluent of methylene chloride and n-hexane in a volume ratio of 1:1.

8. The method of preparing the thermally activated delayed fluorescent material according to claim 2, wherein the step S1 is performed under an inert environment.

\* \* \* \* \*